US012758465B2

(12) United States Patent
Bhushan

(10) Patent No.: US 12,758,465 B2
(45) Date of Patent: Oct. 13, 2026

(54) PERSONAL HYGIENE CAPSULE AND METHODS OF USING SAME

(71) Applicant: ALPHA CLEANTECH LABS INC., Langley (CA)

(72) Inventor: Bharat Bhushan, Langley (CA)

(73) Assignee: ALPHA CLEANTECH LABS INC., Langley (CA)

( * ) Notice: Subject to any disclaimer, the term of this patent is extended or adjusted under 35 U.S.C. 154(b) by 409 days.

(21) Appl. No.: 18/689,032

(22) PCT Filed: Feb. 14, 2022

(86) PCT No.: PCT/CA2022/050210

§ 371 (c)(1),
(2) Date: Mar. 4, 2024

(87) PCT Pub. No.: WO2023/150859

PCT Pub. Date: Aug. 17, 2023

(65) Prior Publication Data

US 2025/0120880 A1 Apr. 17, 2025

(51) Int. Cl.
*E03C 1/01* (2006.01)
*A45D 19/00* (2006.01)
(Continued)

(52) U.S. Cl.
CPC ........... *A61H 35/008* (2013.01); *A45D 19/00* (2013.01); *A47K 1/02* (2013.01); *A47K 7/04* (2013.01); *A61H 9/0021* (2013.01); *A61H 33/005* (2013.01); *A61H 33/6068* (2013.01); *A61H 35/006* (2013.01); *A61L 2/10* (2013.01); *E03C 1/01* (2013.01); *A61H 2009/0035* (2013.01); *A61H 2033/0058* (2013.01); *A61H 2201/0107* (2013.01); *A61H 2201/0111* (2013.01); *A61H 2201/0192* (2013.01);
(Continued)

(58) Field of Classification Search
CPC ................ A61H 35/008; A61H 35/006; A61H 2009/0035; A61H 2001/0107; A45D 19/00; A47K 1/02; A47K 7/04; E03C 1/01
USPC ............................................................ 4/663
See application file for complete search history.

(56) References Cited

U.S. PATENT DOCUMENTS 4,718,131 A * 1/1988 Kitamura ................ A47K 4/00 4/312
5,438,713 A * 8/1995 Clarke ..................... E03C 1/01 4/663
(Continued)

FOREIGN PATENT DOCUMENTS

CN 2153317 Y 1/1994
CN 2710516 Y 7/2005
(Continued)

OTHER PUBLICATIONS www.humanwash.com accessed May 26, 2022.
(Continued)

*Primary Examiner* — Huyen D Le
(74) *Attorney, Agent, or Firm* — Viridant IP

(57) ABSTRACT

A personal hygiene capsule has a housing, a toilet, at least one spray nozzle, a drain provided in a lower portion of the housing, and at least one scrub brush operably mounted to wash at least a portion of an occupant of the personal hygiene capsule. Methods of using the personal hygiene capsule are provided.

17 Claims, 10 Drawing Sheets

(51) Int. Cl.

| | |
|---|---|
| ***A47K 1/02*** | (2006.01) |
| ***A47K 7/04*** | (2006.01) |
| ***A61H 9/00*** | (2006.01) |
| ***A61H 33/00*** | (2006.01) |
| ***A61H 35/00*** | (2006.01) |
| ***A61L 2/10*** | (2006.01) |

(52) U.S. Cl.

CPC ................ *A61H 2201/1619* (2013.01); *A61H 2201/5048* (2013.01); *A61H 2203/0431* (2013.01); *A61H 2205/021* (2013.01); *A61H 2205/12* (2013.01); *A61L 2202/11* (2013.01)

(56) References Cited

U.S. PATENT DOCUMENTS

| | | | | |
|---|---|---|---|---|
| 5,647,074 | A | 7/1997 | White, Jr. et al. | |
| 6,185,759 | B1 * | 2/2001 | Staudenmayer ..... | A47K 17/026 4/663 |
| 6,250,601 | B1 | 6/2001 | Kolar et al. | |
| D487,137 | S * | 2/2004 | Itakura ......................... | D23/274 |
| 6,912,740 | B2 | 7/2005 | Fainberg | |
| 10,278,545 | B2 | 5/2019 | Arab | |
| 2004/0060107 | A1 | 4/2004 | Eisenberg | |
| 2007/0283488 | A1 * | 12/2007 | Birdsall .................... | E03C 1/01 4/622 |
| 2016/0220716 | A1 | 8/2016 | Childress et al. | |
| 2018/0064833 | A1 | 3/2018 | Childress et al. | |
| 2018/0098669 | A1 | 4/2018 | Arab | |
| 2021/0180300 | A1 * | 6/2021 | Brown .................. | A47K 10/32 |

FOREIGN PATENT DOCUMENTS

| | | | |
|---|---|---|---|
| CN | 202636792 | U | 1/2013 |
| CN | 108005415 | A | 5/2018 |
| CN | 108005522 | A | 5/2018 |
| CN | 209058989 | U | 7/2019 |
| CN | 110881884 | A | 3/2020 |
| CN | 215605290 | U | 1/2022 |
| DE | 9311580 | U1 | 11/1993 |
| EP | 0967907 | B1 | 7/2001 |
| JP | H02149577 | A | 12/1990 |
| JP | H06019688 | A | 3/1994 |
| JP | 2007222358 | A | 9/2007 |
| KR | 20120001748 | A | 3/2012 |
| KR | 1020150101293 | A | 9/2015 |
| KR | 102283548 | B1 | 2/2026 |
| WO | 2011143885 | A1 | 11/2011 |
| WO | 2018021899 | A1 | 2/2018 |

OTHER PUBLICATIONS https://www.trendhunter.com/trends/human-washing-machine-avant-santelubain-999-applies-seaweed-packs-too accessed May 26, 2022.

arjo.com/en-us/products/hygiene/ accessed May 26, 2022.

* cited by examiner

PERSONAL HYGIENE CAPSULE AND METHODS OF USING SAME

CROSS-REFERENCE TO RELATED APPLICATIONS

This application is a 371 national phase entry of Patent Cooperation Treaty application No. PCT/CA2022/050210 filed 14 Feb. 2022, entitled PERSONAL HYGIENE CAPSULE AND METHODS OF USING SAME. The foregoing application is hereby incorporated by reference herein in its entirety.

TECHNICAL FIELD

Some embodiments relate to apparatus for facilitating personal hygiene on the part of individuals who are elderly, have reduced mobility, and/or prefer a more automated approach to personal hygiene. Some embodiments relate to methods for effecting personal hygiene in a more automated and independent manner than can be provided by personal care aides.

BACKGROUND

As people age, or for those who suffer from restricted mobility, it may become more and more difficult for a person to carry out basic personal care routines. For example, persons who are disabled or the elderly may require the assistance of a personal care worker to carry out basic routines such as bathing themselves or to assist with toileting. This assistance is difficult for the personal care worker to provide (e.g. being very physical and awkward in nature, particularly for larger individuals), and also represents an invasion of the privacy on the part of the person receiving care. Both of these circumstances may contribute the a person receiving less personal hygiene care than might otherwise be optimal.

Further, the significance of controlling the transmission of communicable diseases to vulnerable residents of assisted living was greatly highlighted by the COVID-19 pandemic. Many vulnerable elderly people were infected and ultimately died through transmission via infected caregivers. Thus, having options to minimize physical contact between those with limited mobility and caregivers would be desirable.

There are moreover ongoing issues with a shortage of caregivers and personal aid workers, and the costs of employing such personnel are relatively high. Injuries can happen both during transfers and during personal hygiene operations, and frequently there is no sterilization of bathing apparatus between uses.

There is a general desire for improved apparatus, systems and methods to allow individuals with reduced mobility to carry out a greater amount of their personal hygiene routine without the assistance of another person. Further, such apparatus, systems and methods may be useful to persons who are able-bodied but simply want a more automated approach to addressing their personal hygiene needs.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

One aspect provides a personal hygiene capsule having a housing, a toilet, at least one spray nozzle, a drain provided in a lower portion of the housing and at least one scrub brush operably mounted to wash at least a portion of an occupant of the personal hygiene capsule. Additional features such as a sink, optionally a moveable sink, a foot massager, a movable shower head, and a hairwashing station can be provided. The hairwashing station can have scrubbing noodles for massaging a scalp of the occupant. The personal hygiene capsule can be provided with one or more white lights for illumination, and/or with one or more UV lights for sterilization. The personal hygiene capsule can be provided with a digital display screen, which can optionally be a touchscreen device and/or voice activated to control the operation of the personal hygiene capsule.

Methods of operating the personal hygiene capsule can be provided, which can include opening doors of the personal hygiene capsule, optionally activating lights, optionally extending a ramp, allowing an occupant to enter the personal hygiene capsule, optionally retracting the ramp, and closing the doors of the personal hygiene capsule. Once inside, an occupant may use voice and/or touchscreen commands to initiate any of a plurality of operating cycles to use the toilet, initiate a bodywash cycle, initiate a tooth and/or face cleaning cycle, a hairwashing cycle, a foot massaging cycle, a drying cycle, a hair drying cycle, or so on. The display screen can optionally be used to provide audio and/or audiovisual entertainment to the occupant.

After an occupant has exited the personal hygiene capsule, washing and/or sterilizing cycles can be provided to clean and/or sterilize the capsule between occupants. Emergency cycles can be initiated based on the doors unexpectedly opening during a cycle, voice commands, or activation of an emergency stop function on the touchscreen display screen. Initiation of the emergency cycle can alert an attendant and/or caregiver that assistance is required.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

DESCRIPTION

Figure 1:
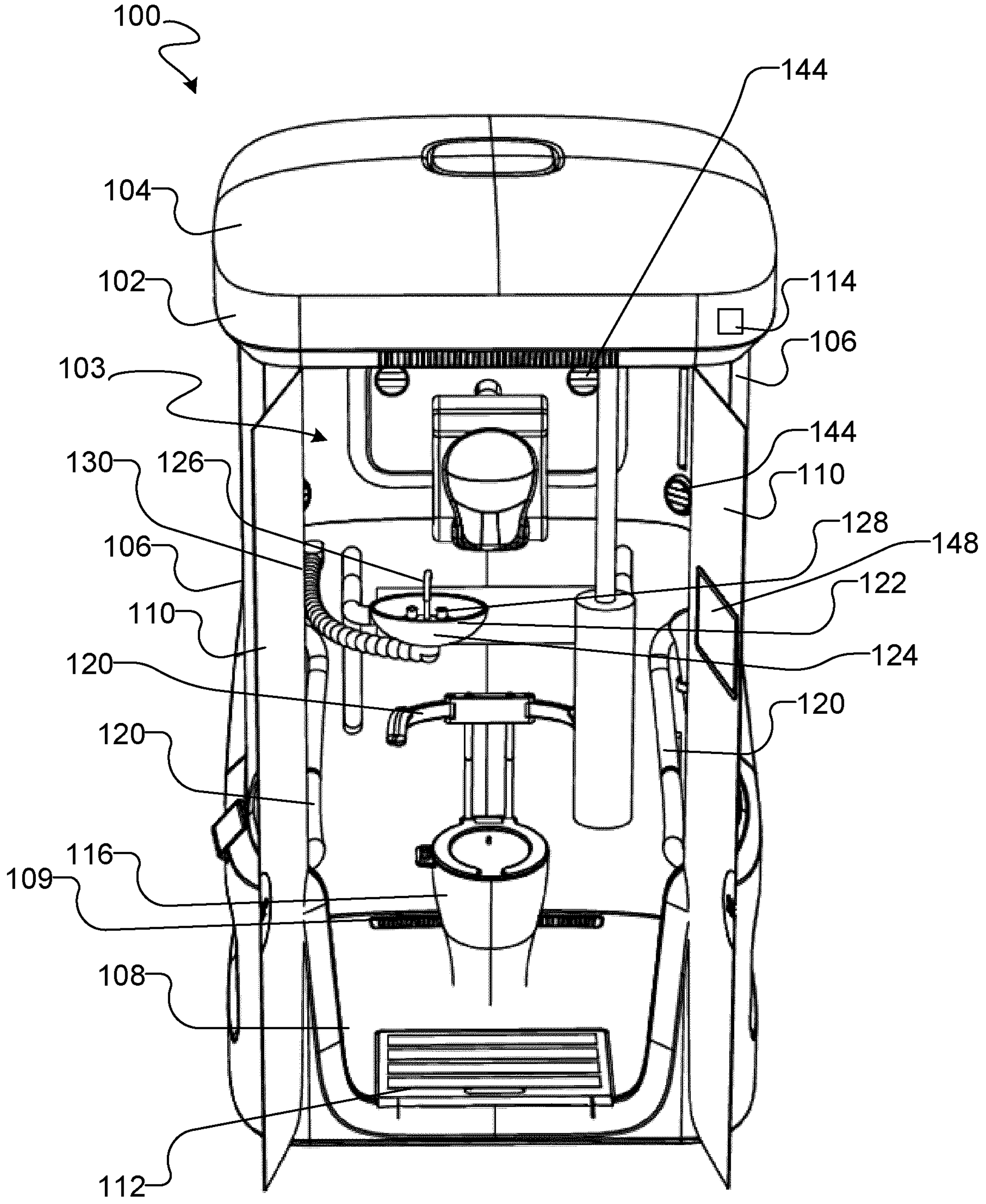
FIG. 1 illustrates a perspective view of a personal hygiene capsule with the doors open.

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

The present invention provides an apparatus and method for automated personal hygiene using a hygiene capsule. The hygiene capsule can be provided with various personal care apparatus such as a toilet, sink or mouth wash station, hair wash station, body scrub brushes, foot cleanser/massager, spray nozzles and/or drying vents. Certain aspects of the operation of the hygiene capsule may be mechanized and/or automated. An infotainment screen may be provided inside the hygiene capsule. A door, entry ramp, grab handles, and appropriate supports such as a back support may be provided to facilitate use of the hygiene capsule by an occupant. The hygiene capsule may be capable of self cleaning and/or self sterilization, for example by using spray nozzles, soap dispensers, drying vents and/or ultraviolet lights. A computer processor may be provided for operating some or all aspects of the hygiene capsule. The computer processor may receive voice commands from an occupant to trigger different functions of the hygiene capsule.

The occupant can select functions of the hygiene capsule, for example using voice-commands, which engage pre-programmed functions directed to individual functions of the hygiene capsule or any combination of functions including, but not limited to: flushing the toilet; bathing or showering and drying an occupant; washing, rinsing, and/or drying an occupant's hair; massaging an occupant's feet; and controlling what is displayed on the information and entertainment system. In some embodiments, the hygiene capsule functions are engaged by a third party, such as a caretaker, via a mobile application. In some embodiments, the operation of the hygiene capsule may be halted by a third party, such as a caretaker, using a mobile application, in response to an alert that the occupant of the hygiene capsule may require assistance.

Because the operation of the hygiene capsule is highly automated, the personal hygiene capsule represents a step towards the automation and/or use of artificial intelligence to carry out personal hygiene functions for those in need of or desiring such assistance.

With reference to FIGS. 1-5, in one embodiment a personal hygiene capsule 100 is provided having an exterior structure 102 to enclose the functional features of the personal hygiene capsule 100 within an interior chamber 103. In the illustrated embodiment, exterior structure 102 is provided by a roof 104, three walls 106, a floor 108, and a door 110. In some embodiments, including the illustrated embodiment, the exterior structure 102 is watertight and door 110 can be placed in watertight engagement with the exterior structure 102, e.g. to contain water dispersed within interior chamber 103 therein.

In some embodiments, a ramp 112 is provided, to facilitate ease of entry or wheelchair accessibility of interior chamber 103. Ramp 112 can be extendible into an extended configuration where ramp 112 projects outwardly from interior chamber and outside of exterior structure 102 to allow for use, and then retractable into a retracted configuration in which ramp 112 is contained within interior chamber 103 so that door 110 can be closed.

In some embodiments, a drain 109 is provided to allow water that is dispensed within interior chamber to be removed from personal hygiene capsule 100. In some embodiments, floor 108 slopes gently towards drain 109, e.g. at an angle of between about 0.5° and 5° from the horizontal, including any value therebetween e.g. 1°, 2°, 3° or 4°, to facilitate the flow of water across floor 108 and into drain 109.

In some embodiments, the personal hygiene capsule 100 is dimensioned to accommodate a single occupant. In some embodiments, the personal hygiene capsule 100 is dimensioned to accommodate a single occupant, and also an assistant such as a care aide, who can help the single user position themselves within the interior chamber 103 as described below.

In this specification, "occupant" refers to a person occupying the interior chamber 103 of the hygiene capsule for the purpose of utilizing the personal hygiene aspects of personal hygiene capsule 100.

Door 110 is openable and closeable to provide access to interior chamber 103 of personal hygiene capsule 100. In some embodiments, door 110 is an automatic door triggered by a proximity sensor or other signal. In some embodiments, floor 108 and/or ramp 112 are made from a non-slip material and/or are coated with a non-slip coating or otherwise provided with surface features to reduce the likelihood of an occupant slipping and falling while utilizing personal hygiene capsule 100.

In some embodiments, ramp 112 is extensible and retractable, so that ramp 112 can be extended automatically or folded out to facilitate entry of the occupant into interior chamber 103. In some embodiments, ramp 112 is an appropriate width to accommodate a wheelchair, and provides an inclined surface to allow the wheelchair to wheel up ramp 112 (e.g. an angle of up to about 45° from horizontal, including e.g. 5°, 10°, 15°, 20°, 25°, 30°, 35° or 40° from horizontal).

In some embodiments, at least one status indicator light, illustrated schematically as 114, is located on the exterior of personal hygiene capsule 100 to indicate the status of the capsule, for example whether it is vacant, occupied or in self-cleaning mode. Status indicator light 114 may, in some embodiments, emit different colors to indicate different statuses of the hygiene capsule. For example, status indicator light 114 may be green to indicate that the personal hygiene capsule 100 is available for use, and red to indicate that personal hygiene capsule 100 is not available for use. Status indicator light 114 may indicate when personal hygiene capsule 100 is vacant, occupied and/or is running a specific pre-programmed function such as those described below. In alternative embodiments, other modes of indicating the status of personal hygiene capsule 100 could be used, for example a manual dial, audible indicia such as a pre-recorded message confirming the status of the capsule, or the like.

In some embodiments, personal hygiene capsule 100 includes various features to enable an occupant to carry out certain personal hygiene routines. For example, in the illustrated embodiment of FIG. 1, a toilet 116 is provided so that an occupant can evacuate their bladder and/or bowel while using personal hygiene capsule 100. In some embodiments, a user can also remain seated on toilet 116 while utilizing other personal hygiene features of capsule 100, as described below. In some embodiments, toilet 116 is self-flushing, for example by being activated to flush by a motion sensor that senses when an occupant has stood up from toilet 116. In some embodiments, toilet 116 includes a bidet feature to assist with cleaning an occupant.

In some embodiments, toilet 116 is provided with a back support 118, which helps to support an occupant in a seated position on toilet 116 and also to prevent the occupant from falling or tilting off toilet 116. In the illustrated embodiment, grab handles 120 are provided, which can be grasped by an occupant to assist in standing from or sitting on toilet 116 as needed.

In some embodiments, personal hygiene capsule 100 is provided with a sink 122. Sink 122 may have a basin 124 for receiving water and/or splashes, a faucet 126 for dispensing water, and handles 128 for regulating water temperature and flow, e.g. conventional hot and cold water taps. In some embodiments, rather than using handles 128 for regulating water temperature and flow, a processing system for receiving voice commands from an occupant may regulate the temperature and flow rate of water supplied to sink 122. In some embodiments, sink 122 may be used to clean an occupant's mouth (e.g. sink 122 may function as a mouth washing station, supplying water for an occupant via handles 128 and faucet 126, and catching splashes using basin 124).

In the illustrated embodiment, sink 122 is attached to one of walls 106 via a flexible arm 130 (which facilitates drainage of used water out of basin 124 and also serves to support sink 122), and may thereby be manually positioned within the interior chamber of the hygiene capsule, e.g. to allow the best positioning for each specific occupant. E.g. when sink 122 is used as a mouth washing station, flexible arm 130 may be used to position sink 122 at a desired position to perform this function. While a rigid arm could be used instead of flexible arm 130 in various embodiments, providing a flexible arm 130 can facilitate entry and exit of an occupant from personal hygiene capsule 100, as sink 122 can be moved away from the occupant during periods when mobility is required (e.g. to a storage position adjacent one of walls 106), and towards the occupant (e.g. to a use position adjacent to the occupant when sated on toilet 116) when the occupant desires to use sink 122. In some embodiments, suitable actuators can be provided as part of flexible arm 130 to allow the positioning of sink 122 within interior chamber 103 to be carried out automatically, for example in response to voice commands issued by an occupant or a helper.

Figure 2:
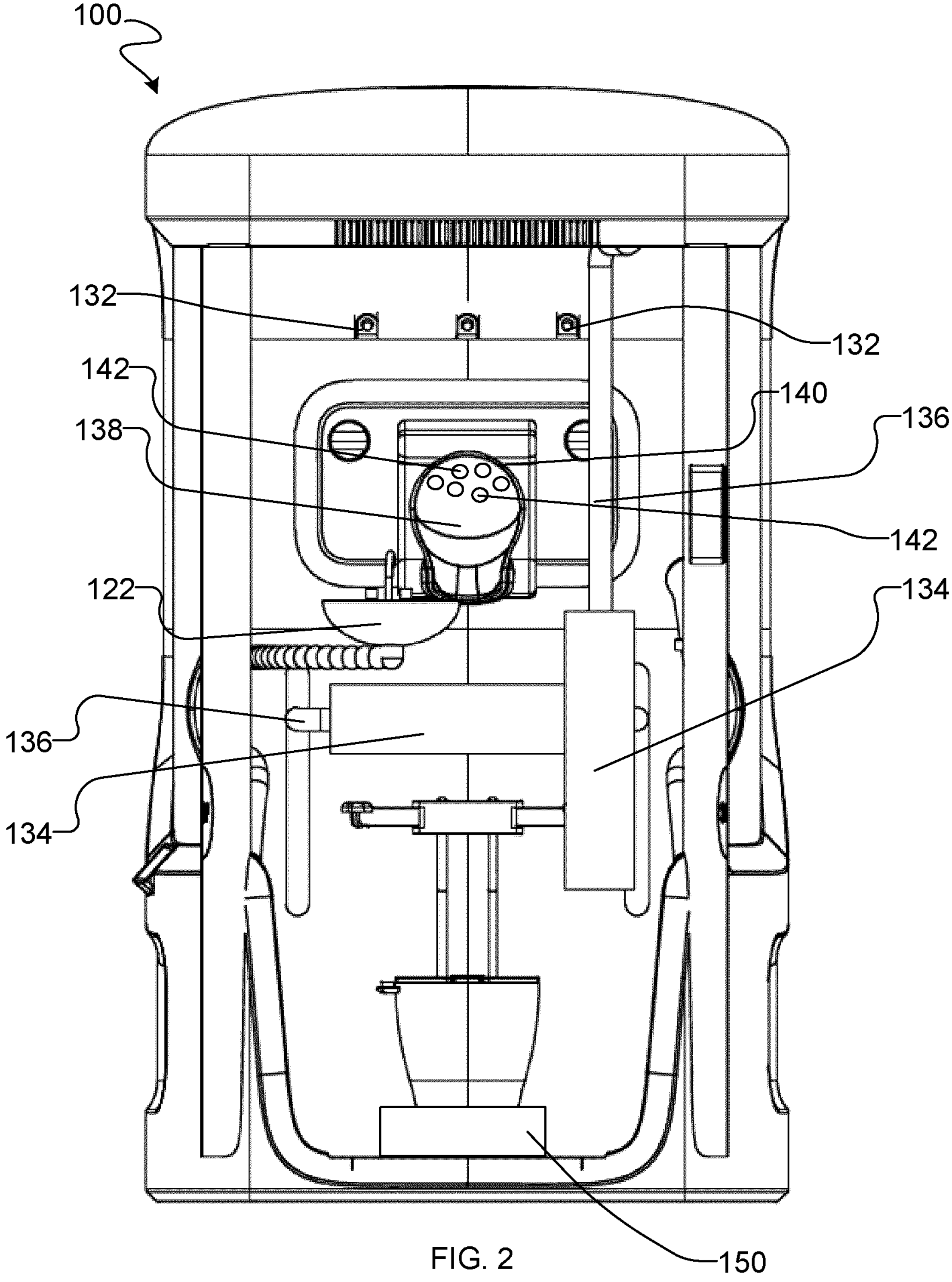
FIG. 2 illustrates a front view of the embodiment illustrated in FIG. 1.
Figure 3:
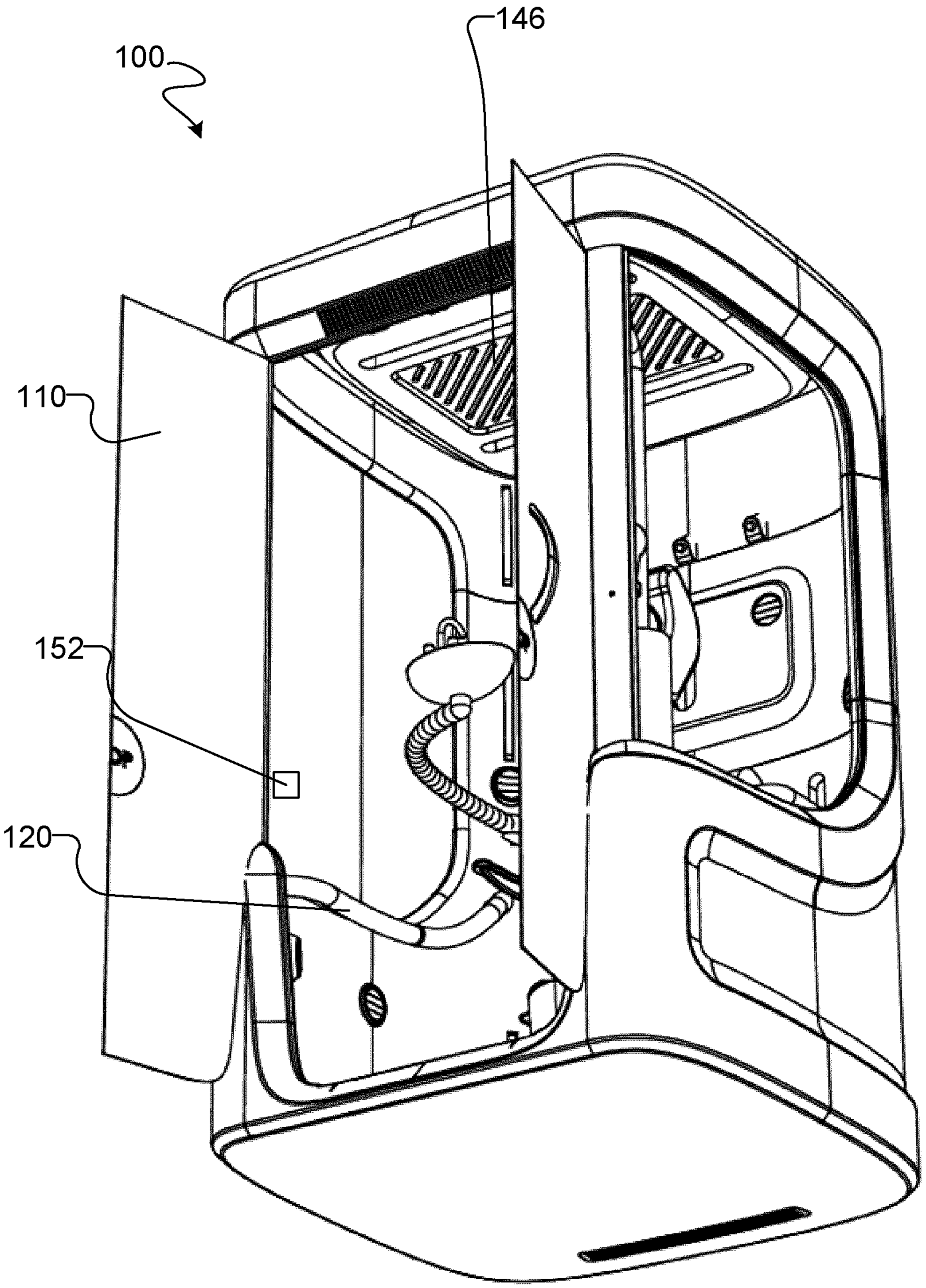
FIG. 3 illustrates a further perspective view of the embodiment illustrated in FIG. 1.
Figure 4:
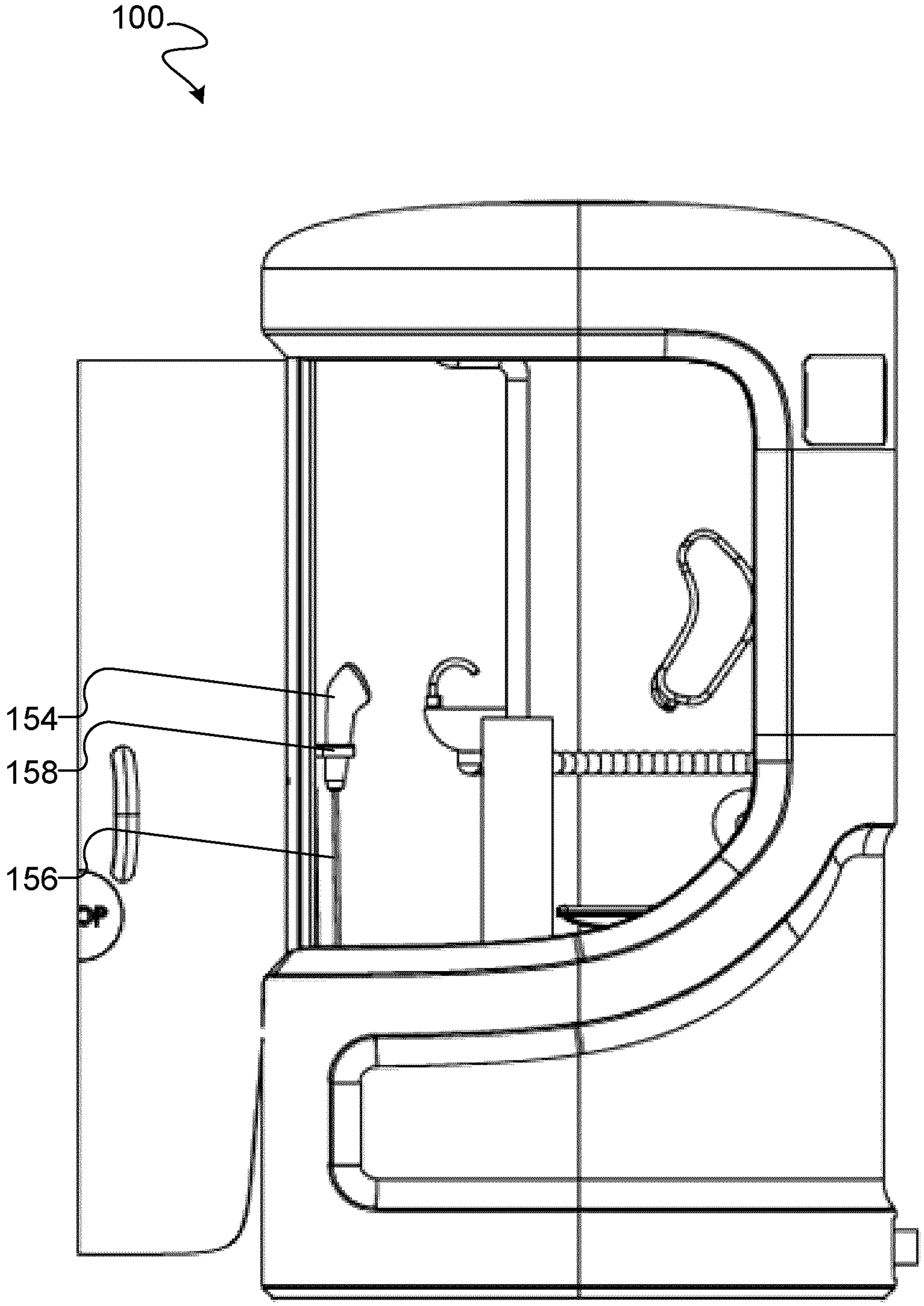
FIG. 4 illustrates a side view of the embodiment illustrated in FIG. 1.
Figure 5:
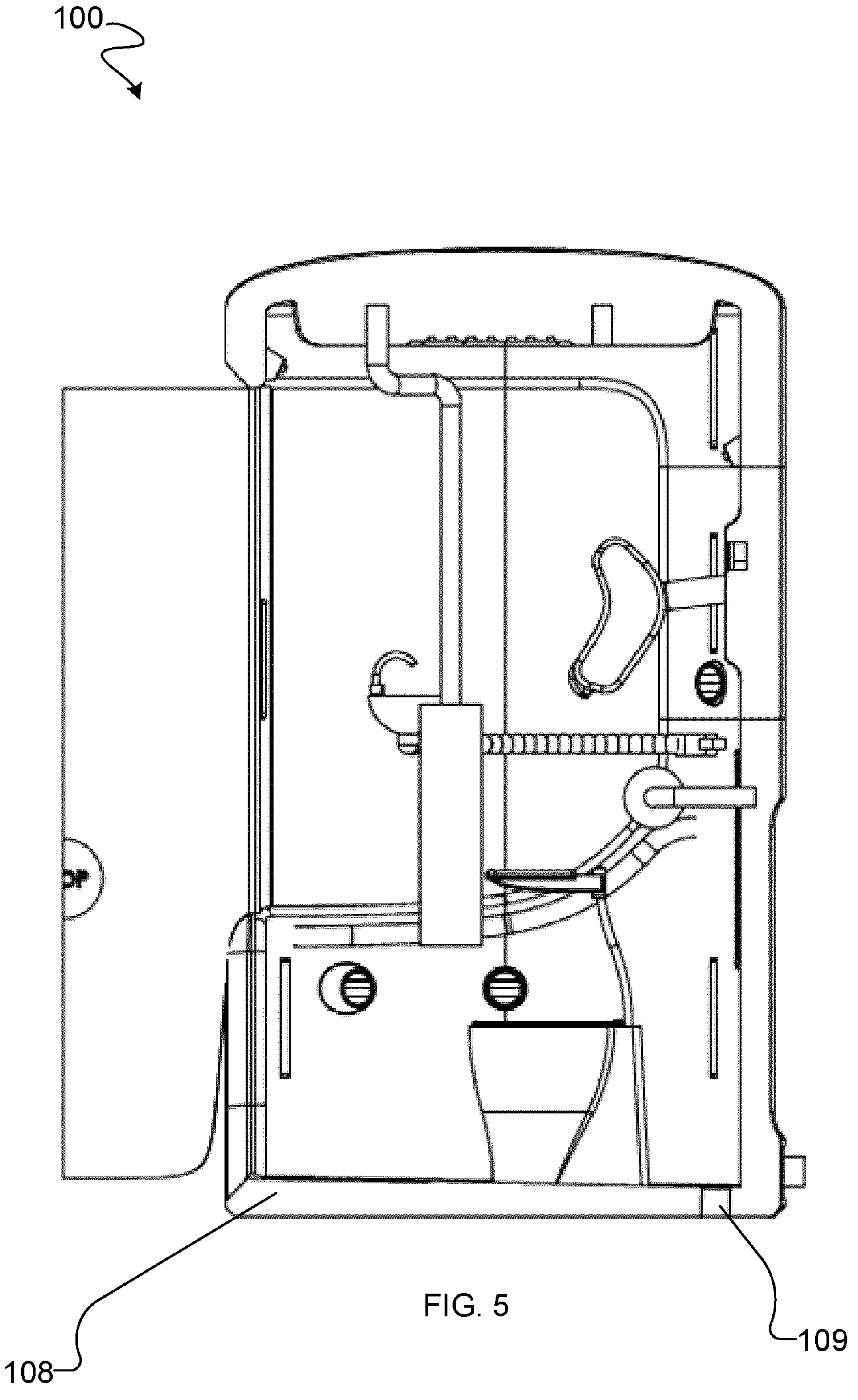
FIG. 5 is a cross-sectional view of the embodiment illustrated in FIG. 1.

With reference to FIG. 2, in some embodiments, personal hygiene capsule 100 includes units configured to wash one or more parts of the body of a user. For example, for general body cleansing, one or more spray nozzles 132 are provided which dispense water at a physiologically comfortable temperature and/or soap towards an occupant seated on toilet 116.

Personal hygiene capsule 100 may further include one or more scrub brushes 134 which can be used to scrub the body of an occupant. Scrub brushes 134 are mounted to appropriate actuators 136 that couple to exterior structure 102 to enable scrub brushes 134 to be manipulated so as to wash various parts of an occupant's body, and to move towards and away from the occupant to facilitate entry and egress of the occupant. In the illustrated embodiment, two scrub brushes 134 are provided, one of which is a horizontally oriented scrub brush positioned to the rear of toilet 116, which can be actuated vertically up and down and can be used in particular to clean an occupant's back, and one of which is a vertically oriented scrub brush which can be rotated about a user as well as actuated vertically up and down to clean the sides, front and legs of an occupant. In the illustrated embodiment, scrub brushes 134 are shown as being generally cylindrical in shape, but other shapes such as contoured, convex, concave or the like could be used in other embodiments. In some embodiments, actuators 136 can be driven by appropriate motors to rotate scrub brushes 134 and move scrub brushes 134 within interior chamber 103. In other embodiments, actuators 136 can rotate scrub brushes 134 but be resiliently flexible, to allow an occupant to move and manipulate the positioning of scrub brushes 134 within interior chamber 103.

In some embodiments, personal hygiene capsule 100 further includes a hairwashing station 138. Hairwashing station 138 has a dome structure 140 dimensioned to accommodate a person's head and is equipped with scrubbing elements, shown schematically as 142, which line the inside of dome structure 140, for washing and rinsing hair. Dome structure 140 of the hair washing station 138 may be may be manually positioned within the interior chamber of the hygiene capsule to be placed above the head of an occupant, and may be adjustable in position to accommodate for the varying heights of different occupants. Water, shampoo, or other liquids and reagents are delivered through dome structure 140 of the hairwashing station 138 for wetting, washing, and rinsing a person's hair.

In some embodiments, one or more air vents 144 are provided. Air can be forced through air vents 144 to assist in drying an occupant after bathing functions have been completed. The air can be at any desired temperature, e.g. slightly heated to ensure that the occupant dries quickly and remains warm.

In some embodiments, one or more lights 146 are provided. In some embodiments, light 146 provides conventional white light, to illuminate interior chamber 103 for an occupant. In some embodiments, light 146 provides ultraviolet light, to assist in sterilizing interior chamber 103 after use. In some embodiments, light 146 provides both white light and ultraviolet light (for example by being provided with two different light sources that can be selectively activated), so that as appropriate light 146 can be used to either provide white light for illumination or ultraviolet light for sterilization.

In various embodiments, air vents 144 and lights 146 can be provided at any or multiple different desired locations within interior chamber 103, for example, in walls 106, roof 104, floor 108 and/or door 110.

In some embodiments, a digital screen 148 is provided within interior chamber 103. In some embodiments, including the illustrated embodiment, digital screen 148 is mounted on an interior surface of door 110, so as to be readily visible to an occupant using personal hygiene capsule 100. Digital screen 148 can be any suitable type of digital screen, for example a tablet, and may act as an infotainment screen, to provide entertaining and/or informative visual content while an occupant is using personal hygiene capsule 100. For example, in some embodiments, digital screen 148 can display information about the status or stage of operation of personal hygiene capsule 100, which could include e.g. the amount of time remaining before a personal hygiene routine is completed.

In some embodiments, digital screen 148 is controlled by voice commands. In other embodiments, digital screen 148 could be operated as a touchscreen device or in any other suitable manner. In some embodiments, digital screen 148 is associated with a virtual assistant software such as Amazon's Alexa, Apple's Siri, or Google Assistant.

In some embodiments, digital screen 148 can have audio capabilities, or personal hygiene capsule 100 can otherwise be provided with suitable speakers or other audio devices, so that an occupant can enjoy audio and/or audiovisual content while using personal hygiene capsule 100 (e.g. by playing movies, music, news, television programs, podcasts, or the like).

In some embodiments, digital screen 148 is waterproof, to avoid damage while personal hygiene capsule 100 is in use. In some embodiments, digital screen 148 itself is not necessarily waterproof, but is mounted within a watertight enclosure provided in interior chamber 103.

In some embodiments, a foot massager 150 is provided within personal hygiene capsule 100. In some embodiments, foot massager 150 is readily removable and re-insertable onto floor 108, and/or can be retracted within a recessed cavity provided in floor 108, so that foot massager 150 will not interfere with ingress and egress of an occupant, particularly an occupant using a wheelchair. For example, foot massager 150 is illustrated in a use position in FIG. 2, but has been removed and is not shown in the remaining figures. Foot massager 150 may be provided with appropriate water jets and/or scrubbing brushes or massaging fingers as may be desired to facilitate cleaning and/or massage of an occupant's feet while personal hygiene capsule 100 is in use.

In some embodiments, personal hygiene capsule 100 is provided with an emergency shut off switch or button, illustrated schematically as 152. An occupant may actuate emergency shut off switch 152 if for any reason the occupant becomes distressed. Emergency shut off switch 152 may also be configured to alert a caregiver that emergency shut off switch 152 has been actuated and ensure that the caregiver is notified to promptly attend to the occupant.

In some embodiments, personal hygiene capsule 100 is provided with a showerhead 154. Showerhead 154 may be attached to a hose 156 and removably supported by a support 158 so that an occupant can lift showerhead 154 from support 158 and direct a flow of water from showerhead 154 wherever may be desired by the occupant. Hose 156 can be suitably plumbed into a supply of water within personal hygiene capsule 100 to supply water to showerhead 154.

In various embodiments, personal hygiene capsule 100 carries out various functions including, but not limited to: flushing the toilet 116; bathing or showering and drying an occupant; washing, rinsing, and/or drying an occupant's hair; and/or massaging an occupant's feet.

In some embodiments, the status of personal hygiene capsule 100 is indicated via status indicator light 114. For example, status indicator light 114 may be green when personal hygiene capsule 100 is ready for use, or red to indicate that personal hygiene capsule 100 is not yet ready for use (for example because a cleaning and sterilization sequence is still in progress).

Figure 6:
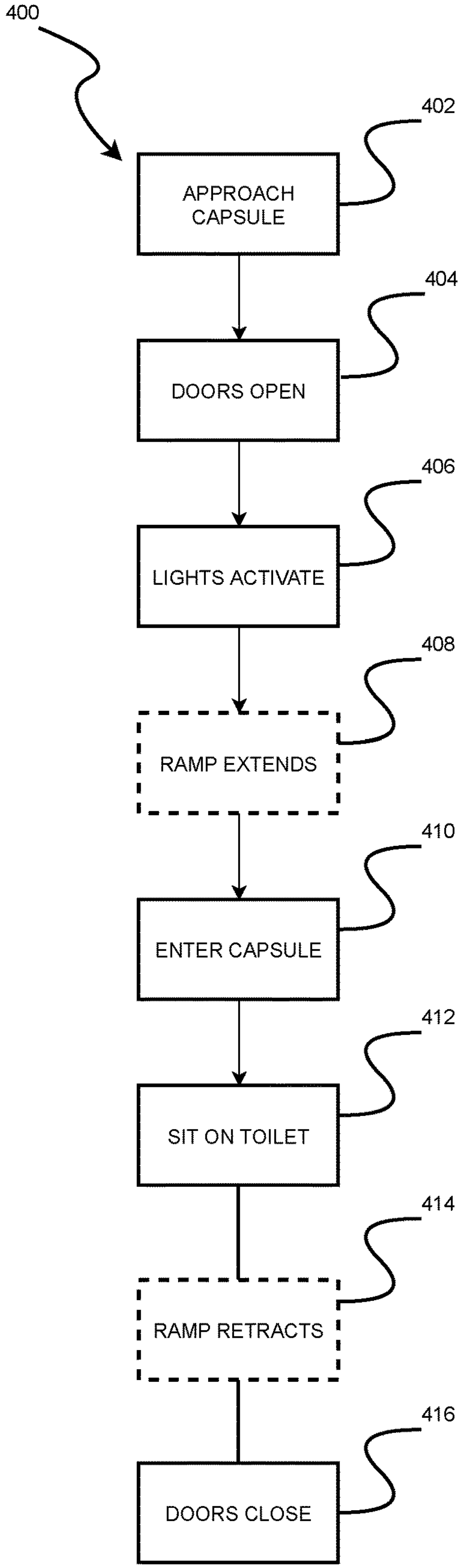
FIG. 6 is an example embodiment of an entry cycle for entering a personal hygiene capsule.

Personal hygiene capsule 100 can be used to carry out various cycles, which can be used alone or combined in various different ways to carry out appropriate personal hygiene routines for an occupant. For example, with reference to FIG. 6, an example embodiment of an entry cycle 400 for an occupant to enter personal hygiene capsule 100 is illustrated.

At 402, an occupant approaches personal hygiene capsule 100. In some embodiments in which door 110 is an automatic door, a proximity sensor is triggered when an occupant approaches door 110 and door 110 opens automatically at 404 to allow the occupant to enter. In alternative embodiments, door 110 could be manually opened at 404 or door 110 could be otherwise activated in any suitable manner, e.g. through a voice command, depressing an appropriate button, or the like. In some embodiments, door 110 could by default be in the open position when personal hygiene capsule 100 is unoccupied and ready for use, so that a step of opening door 110 is not required.

At 406, one or more lights 146 can be turned on, to illuminate interior chamber 103 for the occupant. Lights 146 can be turned on by the control system that controls the operation of personal hygiene capsule 100, or via a conventional light switch, voice command, or in any other suitable manner.

At 408, if the personal hygiene capsule 100 is equipped with a ramp 112 and the occupant wishes to utilize ramp 112 (for example because the occupant is in a wheelchair or has difficulty stepping directly into interior chamber 103), ramp 103 can be actuated to an extended configuration in which it extends outwardly from interior chamber 103, for example upon issuance of a voice command, pressing an appropriate button, or via manual extension by a care aide or other assistive person.

At 410, the occupant enters interior chamber 103, and at 412 the occupant sits on toilet 116 in a conventional fashion. The occupant may use grab handles 120 if desired to assist with entering personal hygiene capsule 100 and positioning themselves on toilet 116, or alternatively a caregiver may assist. At 414, if ramp 112 has been extended, then ramp 414 is moved back to its retracted position, so that doors 110 can be closed at 416.

Figure 7:
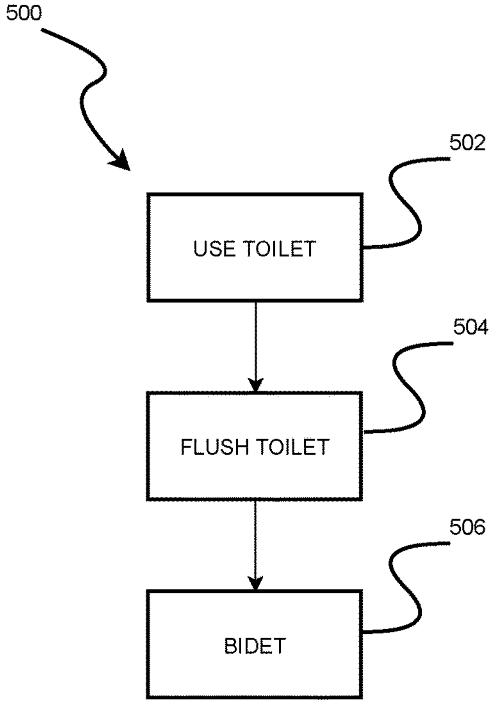
FIG. 7 is an example embodiment of a toilet cycle for a personal hygiene capsule.

With reference to FIG. 7, an example embodiment of a toilet cycle 500 is illustrated. Toilet cycle 500 occurs after an occupant has entered interior chamber 103 by following method 400, but other cycles could occur before toilet cycle 500 occurs after an occupant is inside interior chamber 103 if desired.

At 502, the occupant utilizes toilet 116 for normal toileting functions. At 504, the occupant actuates toilet 116 to cause toilet 116 to flush. In some embodiments, a voice command such as "flush" is used at 504 to cause toilet 116 to flush. In some embodiments, a conventional lever can be actuated to cause toilet 116 to flush, or toilet 116 can be activated in any other suitable manner to cause toilet 116 to flush.

At 506, if equipped and if desired, the bidet function of toilet 116 is activated. For example the bidet function could be activated by a user using a lever in conventional manner, or in embodiments that are more automated, the software that controls the operation of toilet 116 is programmed to activate the water spray from the bidet function of toilet 116 for a predetermined period of time.

Figure 8:
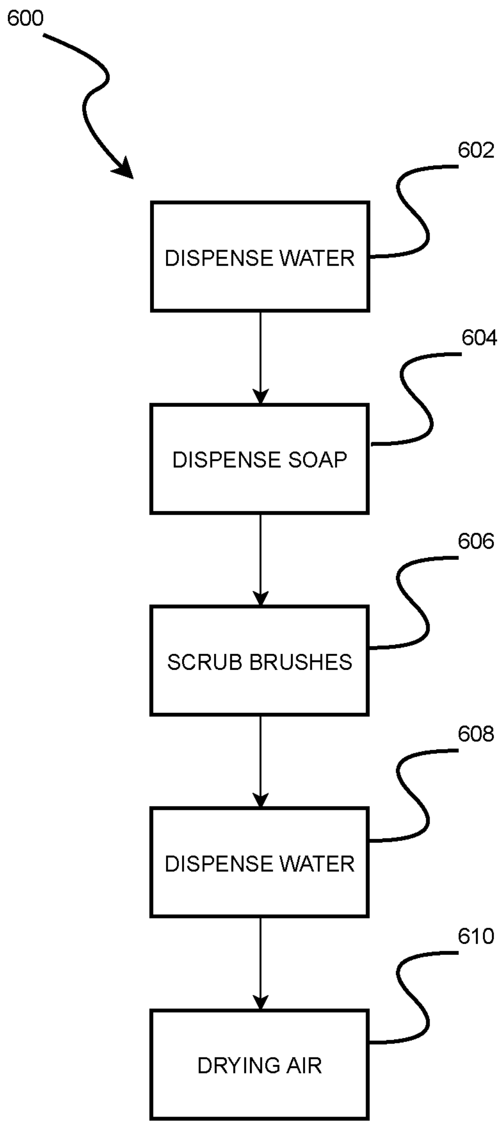
FIG. 8 is an example embodiment of a bath cycle for a personal hygiene capsule.

With reference to FIG. 8, an example embodiment of a bath cycle 600 is illustrated. Bath cycle 600 occurs after an occupant has entered interior chamber 103 by following method 400, but other cycles could occur before bath cycle 600 occurs after an occupant is inside interior chamber 103 if desired.

At 602, water is dispensed via spray nozzles 132 to provide a shower of water over the occupant. The dispensing of water can be stopped at a predetermined time, or in response to a command from an occupant or helper. At 604, soap is dispensed, whether through spray nozzles 132 or through other suitable soap-dispensing nozzles. In some embodiments, soap is sprayed onto the body of the occupant from a plurality of different directions so as to substantially cover most or all of the occupant's body. The dispensing of soap can be stopped at a predetermined time, or in response to a command from an occupant or helper. At 606, scrub brushes 134 are activated so that the occupant's body is scrubbed to assist in effective cleaning. The operation of scrub brushes 134 can be stopped at a predetermined time, or in response to a command from an occupant or helper.

At 608, water is again dispensed via spray nozzles 132 to provide a shower of water over the occupant, to rinse away the soap. The dispensing of water can be stopped at a predetermined time, or in response to a command from an occupant or helper. At any time if an occupant desires and is able, the occupant can optionally also use shower head 154 to manually rinse or cleanse themselves.

At 610, a drying flow of air is provided from air vents 144. The drying flow of air can be stopped at a predetermined time, or in response to a command from an occupant or helper. The air used to provide the drying flow of air can be gently heated, e.g. to a temperature in the range of about 15° C. to about 65° C. including any value therebetween, e.g. 20, 25, 30, 35, 40, 45, 50, 55 or 60° C., to ensure the occupant stays warm throughout the drying process without becoming unduly hot.

Figure 9:
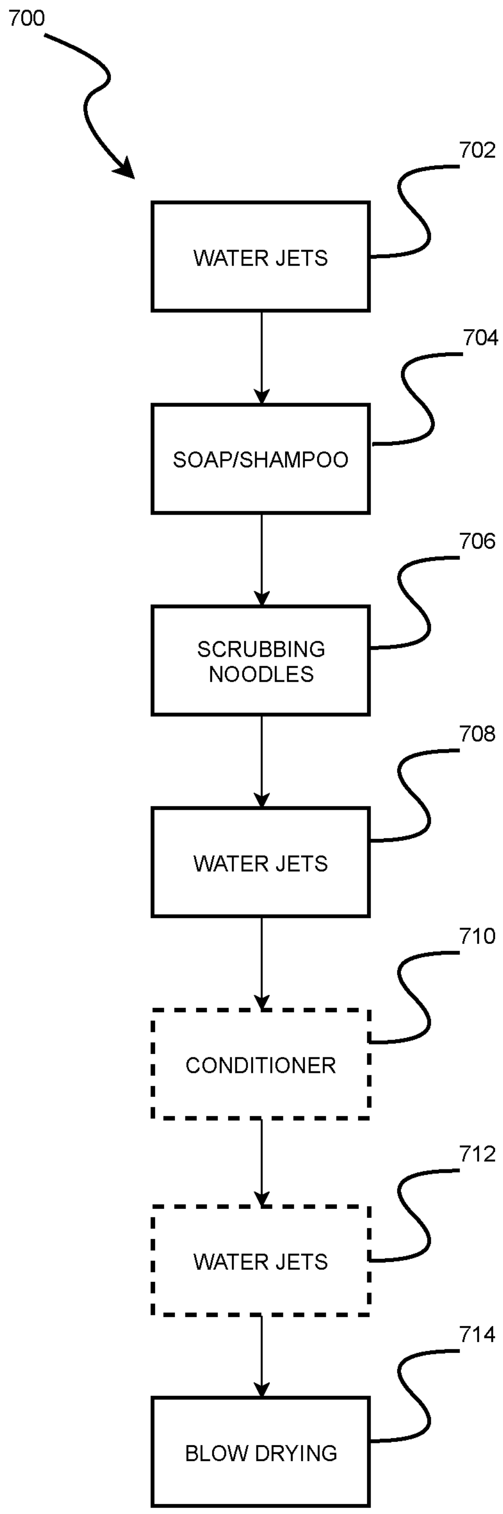
FIG. 9 is an example embodiment of a hair wash cycle for a personal hygiene capsule.

With reference to FIG. 9, an example embodiment of a hair wash cycle 700 is illustrated. At 702, the operation of water jets within hairwashing station 138 is initiated to wet or further wet the occupant's hair. The dispensing of water can be stopped at a predetermined time, or in response to a command from an occupant or helper. Next, at 704, soap or shampoo nozzles provided within hairwashing station 138 so that the soap or shampoo is applied to the occupant's hair. The dispensing of soap/shampoo can be stopped at a predetermined time, or in response to a command from an occupant or helper. At 706, scrubbing noodles within hairwashing station 138 actuate to rub the occupant's hair and scalp to clean the hair. The scrubbing can be stopped at a predetermined time, or in response to a command from an occupant or helper. At 708, the water jets are activated again to rinse the soap/shampoo from the occupant's hair. The dispensing of water can be stopped at a predetermined time, or in response to a command from an occupant or helper. At 710, any desired conditioner or follow-on treatment to the soap/shampoo can be applied via the soap or shampoo nozzles. The dispensing of conditioner can be stopped at a predetermined time, or in response to a command from an occupant or helper. At 712, if conditioner was applied, the water jets are activated again to rinse the conditioner from the occupant's hair. The dispensing of water can be stopped at a predetermined time, or in response to a command from an occupant or helper. At 714, an air blow dryer provided in hairwashing station 138 is used to dry the occupant's hair. The air blown by the air blow dryer can be gently heated, e.g. to a temperature in the range of about 15° C. to about 65° C. including any value therebetween, e.g. 20, 25, 30, 35, 40, 45, 50, 55 or 60° C., to ensure the occupant stays warm throughout the drying process without becoming unduly hot.

In some embodiments, hair wash cycle 700 is operated partway through bath cycle 600, for example prior to or after soap is dispensed at 604. Similarly, drying step 714 of hair wash cycle 700 may be deferred until after water has finished being sprayed at 608, and optionally may be carried out at the same time as drying step 610.

Figure 10:
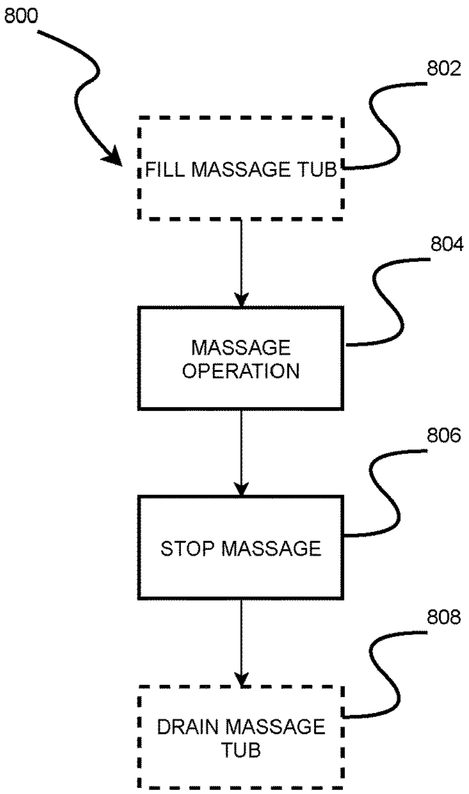
FIG. 10 is an example embodiment of a foot massage cycle for a personal hygiene capsule.

With reference to FIG. 10, an example embodiment of a foot massage cycle 800 is illustrated. At 802, the tub of foot massager 150 may optionally be filled with warm water if desired. At 804, the machinery of foot massager 150 commences operation to provide a massage to the occupant's feet. Once the desired level of foot massage time has been reached, the massaging action may be stopped via any appropriate command input as described below at 806. At 808, if the tub of the foot massager 150 was filled with water, that water is drained from the tub of foot massager 150. In various embodiments, foot massage cycle 800 may be carried out prior to drying step 610 of wash cycle 600, so that the occupant's entire body can be dried. In other embodiments, after completion of foot massage cycle 800 without wash cycle 600 being operated, drying step 610 of cycle 600 could be carried out in isolation to dry the occupant's feet subsequent to foot massage cycle 800 in embodiments in which the tub of foot massager 150 is filled with warm water.

Figure 11:
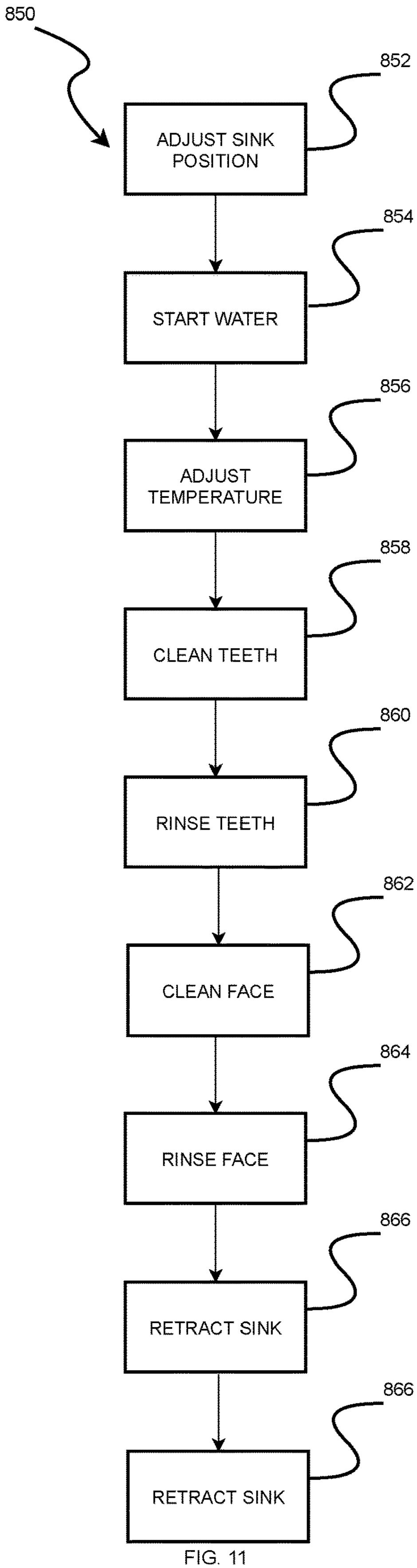
FIG. 11 is an example embodiment of a tooth cleaning and face washing cycle for a personal hygiene capsule.

With reference to FIG. 11, an example embodiment of a tooth cleaning and face washing cycle 850 using sink 122 is illustrated. In some embodiments, only certain steps of cycle 850 might be conducted, e.g. only the steps required to clean teeth, or only the steps required to wash the occupant's face. At 852, the position of flexible arm 130 is adjusted so that sink 122 is positioned comfortably proximate an occupant's face. At 854, the user actuates handles 128 to start a flow of water through faucet 126. At 856, the user optionally adjusts the temperature of the water flowing through faucet 126 to a desired temperature using handles 128. At 858 to clean the occupant's teeth, optionally the occupant can apply toothpaste to the teeth and/or use a toothbrush in conventional fashion to clean the teeth. At 860, the occupant can then use the water flowing through faucet 126 to rinse his or her mouth, with excess water being drained by basin 124.

At 862, to clean the occupant's face, the user can use the water flowing through faucet 126, optionally apply soap from a soap dispenser, and apply friction by rubbing with the occupant's hands. At 864, the occupant can then use the water flowing through faucet 126 to rinse his or her face, allowing excess water to be drained by basin 124. Once the occupant has completed the tooth brushing and/or face washing cycle, at 866, the flow of water through faucet 126 is stopped by actuating handles 128, and at 868, the position of flexible arm 130 is adjusted so that sink 122 is out of the occupant's way.

Figure 12:
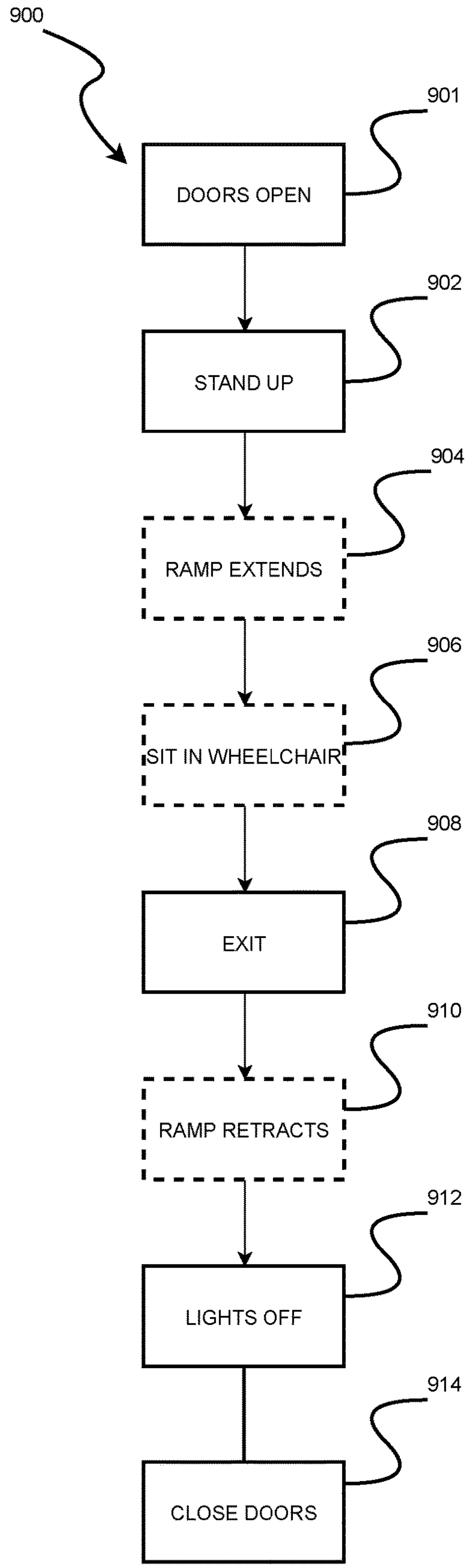
FIG. 12 is an example embodiment of an exit cycle for exiting a personal hygiene capsule.

With reference to FIG. 12, an example embodiment of an exit cycle 900 for exiting personal hygiene capsule 100 after the occupant has finished is illustrated. At 901, door 110 opens. At 902, the occupant stands up off of toilet 116. At 904, ramp 112 is extended in embodiments that are provided with a ramp. At 906, if the occupant uses a wheelchair for mobility, the occupant can sit in their wheelchair, optionally with the assistance of a helper or care aide. At 908, the occupant can exit personal hygiene capsule 100. At 910, the ramp 112 if used is retracted, and at 912, light 146 turns off. At 914, door 110 is closed.

Figure 13:
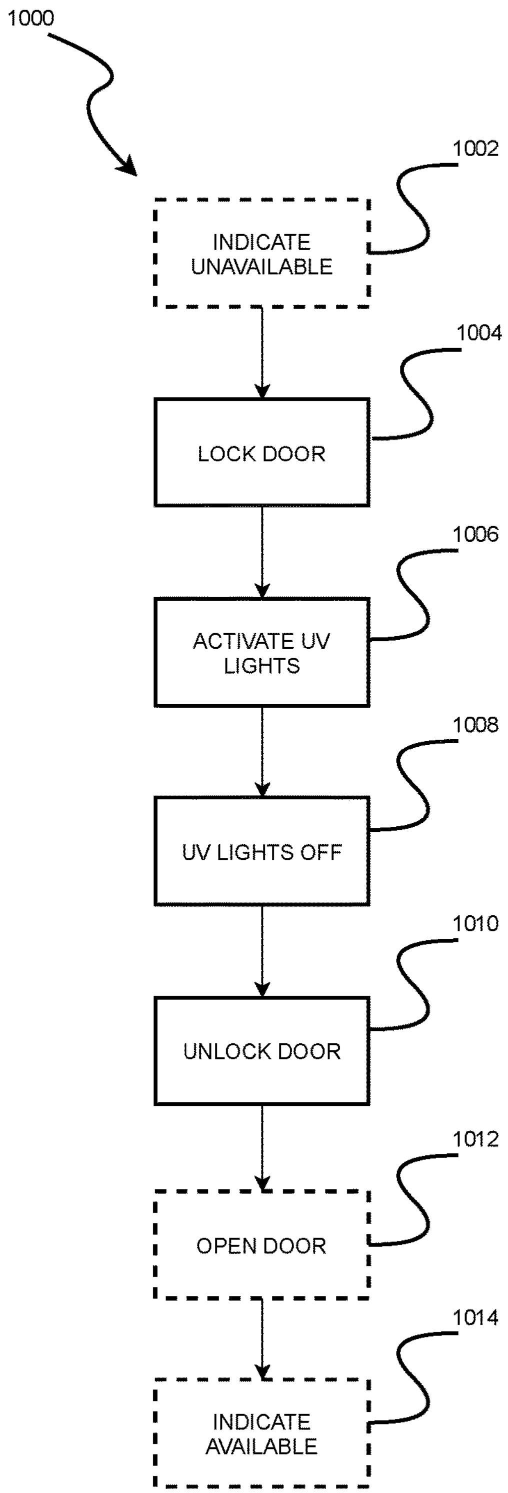
FIG. 13 is an example embodiment of a sterilization/disinfection cycle for a personal hygiene capsule.

After each use, personal hygiene capsule 100 can undergo a sterilization cycle, an example embodiment of which is illustrated as sterilization cycle 1000 in FIG. 13. In some embodiments, sterilization cycle 1000 automatically initiates after an occupant has exited and exit cycle 900. In some embodiments, at 1002, status indicator light 114 is changed to red, so that potential occupants will know that personal hygiene capsule 100 is not available for use. In alternative embodiments, any other suitable indicia could be used, e.g. audible indicia, a display screen, backlit status lights, or the like.

At 1004, door 110 is locked so that a potential occupant does not inadvertently enter personal hygiene capsule 100 during sterilization cycle 1000. In some embodiments, door 110 is locked from the inside, so that it cannot be unlocked during sterilization cycle 1000. At 1006, the UV lights of lights 146 are turned on to initiate the sterilization process by killing or inactivating any microorganisms or viruses which may have been brought inside interior chamber 103 by the previous occupant. After a predetermined period of time sufficient for the desired degree of sterilization (a sterilization period), at 1008 the UV lights of lights 146 are turned off.

At 1010, door 110 is unlocked, and at 1012 if desired door 110 can be opened to facilitate entry of the next occupant. At 1014, status indicator light 114 is changed to green, so that potential occupants will know that personal hygiene capsule 100 is now available for use. In alternative embodiments, any other suitable indicia could be used, e.g. audible indicia, a display screen, backlit status lights, or the like.

Figure 14:
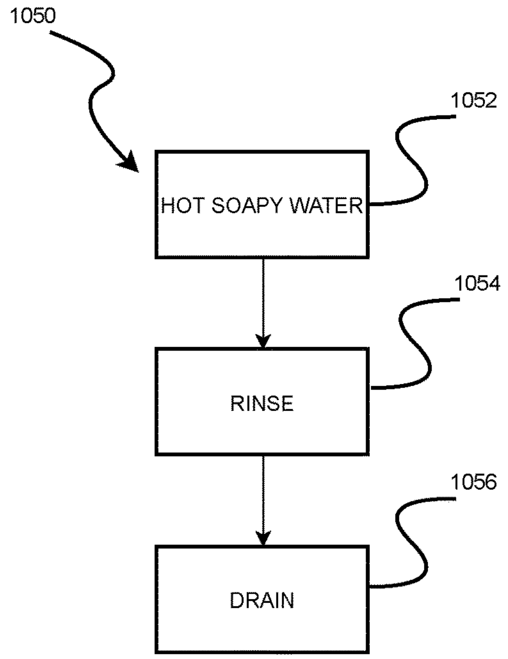
FIG. 14 is an example embodiment of a cleaning cycle for a personal hygiene capsule.

In some embodiments, as illustrated with reference to FIG. 14, in addition to or instead of sterilization cycle 1000, personal hygiene capsule 100 can undergo a physical cleaning cycle 1050 while door 110 is locked as described above for sterilization cycle 1000. At 1052, spray nozzles and soap dispensers within personal hygiene capsule 100 are activated so that the interior surfaces are sprayed with hot soapy water to physically scrub away any dirt or microorganisms. At 1054, any soap dispensers are stopped, while the spray nozzles continue to spray hot water to rinse the interior surfaces of personal hygiene capsule 100. At 1056, any remaining water is permitted to drain out of drain 109.

Figure 15:
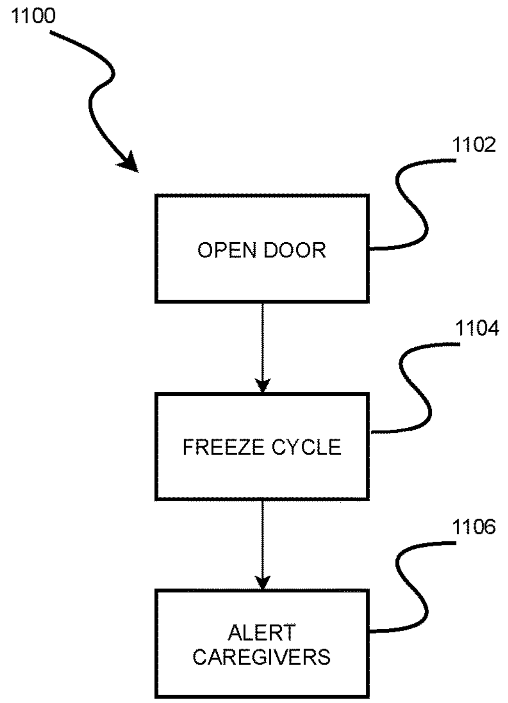
FIG. 15 is an example embodiment of a safety cycle for a personal hygiene capsule.

Appropriate safety systems and/or safety cycles can be incorporated into personal hygiene capsule 100. For example, with reference to FIG. 15, in one example embodiment of a safety cycle 1100, if an occupant opens door 110 at 1102 while any cycle of personal hygiene capsule 100 is in operation, at 1104 the active cycle of the personal hygiene capsule 100 will freeze. At 1106, optionally any appropriate indicia can be activated to alert caregivers that assistance is required, for example status indicator light 114 could be caused to blink red, audible indicia such as an alarm or voice command could be sounded, appropriate notifications such as a paging message or a text message could be sent to a caregiver or emergency contact person at a remote location, or the like.

Figure 16:
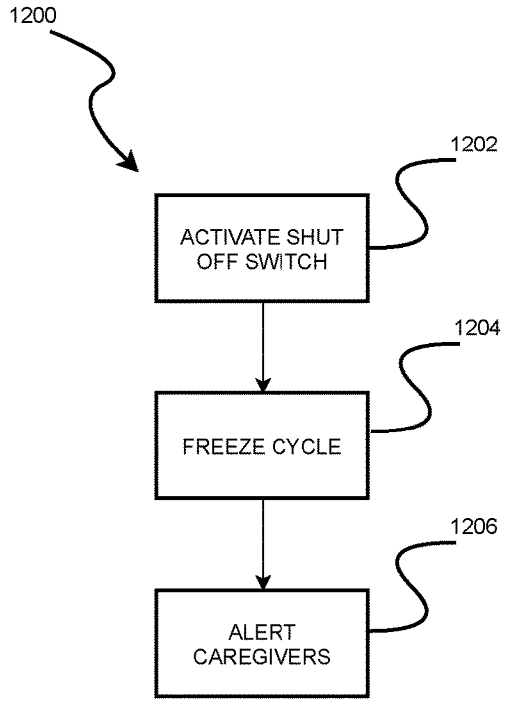
FIG. 16 is another example embodiment of a safety cycle for a personal hygiene capsule.

An alternative embodiment of a safety cycle is illustrated as 1200 in FIG. 16. At 1202, an occupant actuates emergency shut off switch 152. In response, at 1204, any cycle of personal hygiene capsule 100 that is in operation is frozen. At 1206, optionally any appropriate indicia can be activated to alert caregivers that assistance is required, for example status indicator light 114 could be caused to blink red, audible indicia such as an alarm or voice command could be sounded, appropriate notifications such as a paging message or a text message could be sent to a caregiver or emergency contact person at a remote location, or the like.

Other provisions could be made to ensure the safety of an occupant during the various stages of operation of personal hygiene capsule 100. For example, personal hygiene capsule 100 may not perform any functions relating to the personal hygiene of the occupant unless door 110 is in a closed position.

In other embodiments, the user could wear a safety device configured to determine when a user has fallen and/or personal hygiene capsule 100 can be provided with appropriate accelerometers or other devices enabling personal hygiene capsule 100 to sense if an occupant has fallen. If a fall is detected, then an appropriate alert or alarm can be activated so that a caregiver is alerted to the need to check on the safety of the occupant of personal hygiene capsule 100.

In various embodiments, the control of the activation of the various cycles that personal hygiene capsule 100 can perform can be accomplished in any suitable manner. For example, in some embodiments, personal hygiene capsule 100 is configured to accept voice commands to initiate the various cycles and/or specific steps in each cycle for hands-free operation. Voice-activation encompasses using pre-programmed voice commands to start or stop a function of the hygiene capsule or to select specific functions of the hygiene capsule or combinations of functions.

Thus, for example, an occupant could use a voice command such as “flush” to activate the flushing (and optionally bidet function after the flushing of the toilet is completed) functions of toilet 116 during toilet cycle 500. A voice command such as “bath” could be used to initiate bath cycle 600. A voice command such as “hair wash” could be used to initiate hair wash cycle 700. A voice command such as “foot massage” or “massage” could be used to initiate foot massage cycle 800. A voice command such as “wash face” or “clean teeth” could be used to initiate a tooth cleaning and/or face washing cycle 850. At any time, an occupant can use a voice command such as “stop” to halt the current cycle (which might occur after completion of the relevant step in the cycle; for example when toilet 116 is flushing at 504, the flushing step would be completed before the cycle is stopped). A voice command such as “help” could be used to activate a safety cycle equivalent to safety cycles 1100 and 1200. Further, voice commands could be used to operate digital screen 148, e.g. a voice command such as “hello” or a touch on the screen could be used to turn on digital screen 148.

In alternative embodiments, other modes of processing commands from an occupant could be used, for example input via digital screen 148, activation of appropriate buttons, external control by an assistant responsive to requests from the occupant, and so on.

In various embodiments, the operation of each step of the various cycles that personal hygiene capsule 100 can perform can be controlled in any suitable manner. For example, voice commands or other suitable prompts (such as pressing a button or providing input through digital screen 148) can be used by an occupant to advance through each step of a cycle as the occupant determines that the prior step has been completed.

In some embodiments, personal hygiene capsule 100 is automated in that it is equipped with software which runs pre-programmed functions of the hygiene capsule, such as any of cycles 400, 500, 600, 700, 800, 850, 900, 1000, 1050, 1100 or 1200. The pre-programmed functions are directed to individual functions of the hygiene capsule or any combination of functions including, but not limited to: flushing the toilet; bathing or showering and drying an occupant; washing, rinsing, and/or drying an occupant's hair; massaging an occupant's feet; controlling the content displayed on digital screen; and engaging the self-cleaning function of the hygiene capsule. The pre-programmed functions carry out the functions of the hygiene capsule through controlling the operation of the toilet (for example, flushing); the delivery of water, soaps, shampoos, or other liquids and reagents from the nozzles or hair washing apparatus; the delivery of air through the air vents; the movement and rotation of the scrubbing apparatuses; the operation of the foot massaging apparatus; and the content displayed on the digital screen.

In some embodiments, personal hygiene capsule 100 is capable of being remotely operated via a mobile application. In some embodiments, personal hygiene capsule 100 is operated by input into digital screen 148, which may be a touch screen.

Figure 17:
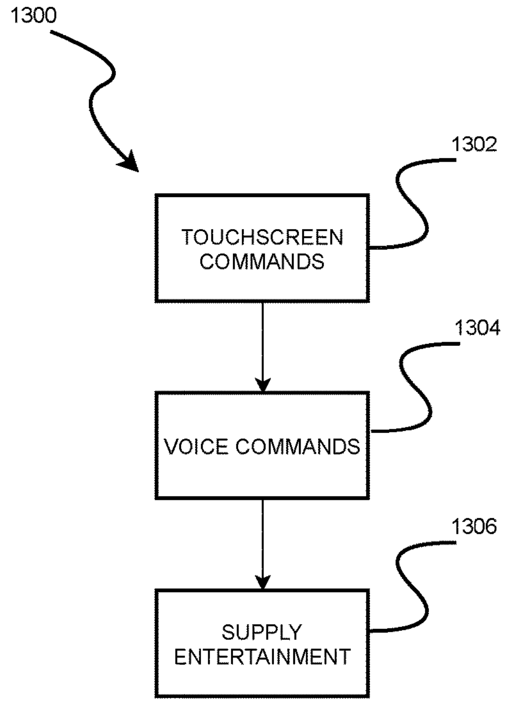
FIG. 17 is an example embodiment of the operation of a digital screen of a personal hygiene capsule.

In some embodiments, as illustrated as 1300 in FIG. 17, digital screen 148 can be operated by touchscreen interactions provided by an occupant or caregiver and/or by voice commands. For example, at 1302, digital screen 148 can display a menu of available cycles such as toilet cycle 500, bath cycle 600, hair wash cycle 700, foot massage cycle 800, tooth cleaning or face washing cycle 850, or any other available cycle. The user can use the touchscreen feature of digital screen 148 to select and initiate the appropriate cycle. At 1304, an occupant can use voice commands to initiate any one of the desired cycles through digital screen 148. At 1306, digital screen 148 may output entertainment for a user, for example in the form of audio and/or audiovisual content such as movies, music, news, television programs, podcasts or the like).

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are consistent with the broadest interpretation of the specification as a whole.

The invention claimed is:

1. A personal hygiene capsule comprising:
- a housing;
- a toilet;
- at least one spray nozzle;
- a drain provided in a lower portion of the housing; and
- at least two scrub brushes operably mounted to the housing to wash at least a portion of an occupant of the personal hygiene capsule, a first one of the at least two scrub brushes comprising a vertically disposed scrub brush mounted to contact at least one side of an occupant when the occupant is in a seated position on the toilet; and
- a sink, wherein the sink is movably mounted on a flexible arm so that the sink can be moved between a use position adjacent to an occupant seated on the toilet and a storage position adjacent a wall of the housing.

2. The personal hygiene capsule as defined in claim 1, wherein a second one of the at least two scrub brushes comprises a horizontally disposed scrub brush mounted rearwardly of the toilet.

3. The personal hygiene capsule as defined in claim 1, wherein the housing comprises a door that is openable and closeable into watertight engagement with the housing, and wherein the housing is watertight.

4. The personal hygiene capsule as defined in claim 1, comprising a back support positioned to support an occupant when the occupant is in a seated position on the toilet.

5. The personal hygiene capsule as defined in claim 1, comprising a hairwashing station positioned and configured to contact hair of an occupant when the occupant is in a seated position on the toilet.

6. The personal hygiene capsule as defined in claim 1, further comprising a movable shower head.

7. The personal hygiene capsule as defined in claim 1 comprising a foot massage unit.

8. The personal hygiene capsule as defined in claim 7, wherein the foot massage unit is optionally retractable within a recessed cavity of a floor of the housing.

9. The personal hygiene capsule as defined in claim 7, wherein the foot massage unit is removable.

10. The personal hygiene capsule as defined in claim 1 comprising a digital display screen mounted within an interior chamber of the housing.

11. The personal hygiene capsule as defined in claim 10, wherein the digital display screen is configured as a touch screen for receiving input from an occupant to operate various functions of the personal hygiene capsule.

12. The personal hygiene capsule as defined in claim 10, wherein the digital display screen comprises an infotainment unit.

13. The personal hygiene capsule as defined in claim 1, wherein the hairwashing station comprises scrubbing noodles for massaging a scalp of the occupant.

14. The personal hygiene capsule as defined in claim 1, wherein the hairwashing station further comprises an air blow dryer.

15. The personal hygiene capsule as defined in claim 1, further comprising one or more lights.

16. The personal hygiene capsule as defined in claim 15, wherein the one or more lights comprise conventional white lights and/or ultraviolet lights.

17. The personal hygiene capsule as defined in claim 1, further comprising grab bars mounted to support a user moving into a seated position on the toilet.

* * * * *